United States Patent [19]

Nagpal et al.

[11] Patent Number: 5,817,160
[45] Date of Patent: Oct. 6, 1998

[54] UV ABSORBING GLASS

[75] Inventors: Vidhu Jaikishen Nagpal; Seshu Babu Desu; Richey McLane Davis, all of Blacksburg, Va.

[73] Assignee: The Center for Innovative Technology, Herndon, Va.

[21] Appl. No.: 646,524

[22] Filed: May 7, 1996

Related U.S. Application Data

[60] Division of Ser. No. 261,900, Jun. 15, 1994, abandoned, which is a continuation-in-part of Ser. No. 991,130, Dec. 16, 1992, abandoned.

[51] Int. Cl.⁶ .............................. C03B 8/00; C03B 19/12
[52] U.S. Cl. .............................. 65/17.3; 65/17.2; 65/901
[58] Field of Search ...................... 65/17.2, 60.5, 65/60.53, 134.1, 134.3, 901, 17.3; 427/160, 193, 215, 218

[56] References Cited

U.S. PATENT DOCUMENTS

| | | | |
|---|---|---|---|
| Re. 33,729 | 10/1991 | Perillou | 359/359 |
| 1,414,715 | 5/1922 | Taylor | 501/64 |
| 1,637,439 | 8/1927 | Coblentz | 501/64 |
| 1,936,231 | 11/1933 | Gelstharp et al. | 106/36.1 |
| 2,444,976 | 7/1948 | Brown | 29/56.5 |
| 2,524,719 | 10/1950 | Tillyer | 106/52 |
| 2,860,059 | 11/1958 | Molter et al. | 106/52 |
| 3,652,303 | 3/1972 | Rao | 106/52 |
| 4,038,228 | 7/1977 | Taylor | 536/64 |
| 4,057,408 | 11/1977 | Pierson et al. | 65/18 |
| 4,275,118 | 6/1981 | Baney et al. | 428/412 |
| 4,278,632 | 7/1981 | Yoldas | 264/66 |
| 4,349,456 | 9/1982 | Sowman | 252/317 |
| 4,534,892 | 8/1985 | Suzuki et al. | 252/545 |
| 4,571,361 | 2/1986 | Kawaguchi et al. | 428/428 |
| 4,680,048 | 7/1987 | Motoki et al. | 65/17.2 |
| 4,704,425 | 11/1987 | Lagarde et al. | 524/492 |
| 4,726,828 | 2/1988 | Clasen | 65/396 |
| 4,741,931 | 5/1988 | Lin et al. | 427/387 |
| 4,753,827 | 6/1988 | Yoldas et al. | 427/387 |
| 4,754,012 | 6/1988 | Yoldas et al. | 528/10 |
| 4,772,436 | 9/1988 | Tyszblat | 264/19 |
| 4,786,619 | 11/1988 | Gerrard et al. | 501/64 |
| 4,792,536 | 12/1988 | Pecoraro et al. | 501/70 |
| 4,799,963 | 1/1989 | Basil et al. | 106/287.13 |
| 4,801,445 | 1/1989 | Fukui et al. | 424/69 |
| 4,814,017 | 3/1989 | Yoldas et al. | 106/287.12 |
| 4,839,454 | 6/1989 | Lin et al. | 528/32 |
| 5,006,248 | 4/1991 | Anderson et al. | 210/500.25 |
| 5,030,097 | 7/1991 | Tobey | 433/199.1 |
| 5,035,745 | 7/1991 | Lin et al. | 106/287.16 |
| 5,077,133 | 12/1991 | Cheng | 428/426 |
| 5,147,125 | 9/1992 | Austin | 359/359 |
| 5,209,863 | 5/1993 | Dixit et al. | 252/94 |
| 5,227,342 | 7/1993 | Anderson et al. | 501/12 |
| 5,245,486 | 9/1993 | Demiryont et al. | 359/359 |
| 5,249,076 | 9/1993 | Fujiwara et al. | 359/350 |
| 5,316,854 | 5/1994 | Lin et al. | 428/426 |
| 5,344,712 | 9/1994 | Basil et al. | 428/412 |
| 5,464,462 | 11/1995 | Langer et al. | 65/66 |

*Primary Examiner*—Donald E. Czaja
*Assistant Examiner*—Sean Vincent
*Attorney, Agent, or Firm*—Conley, Rose & Tayon, P.C.

[57] ABSTRACT

UV absorbing glass is prepared by mixing ultrafine colloidal cerium oxide with glass-forming substances during the fabrication of the glass. An aqueous colloidal dispersion containing 1–20 weight percent 10–20 nm cerium oxide particles, optionally including a binder, is admixed with silica sand, and the sand is dried, melted and cooled to give a relatively clear UV absorbing glass containing 0.3–2 weight percent cerium oxide.

1 Claim, 8 Drawing Sheets

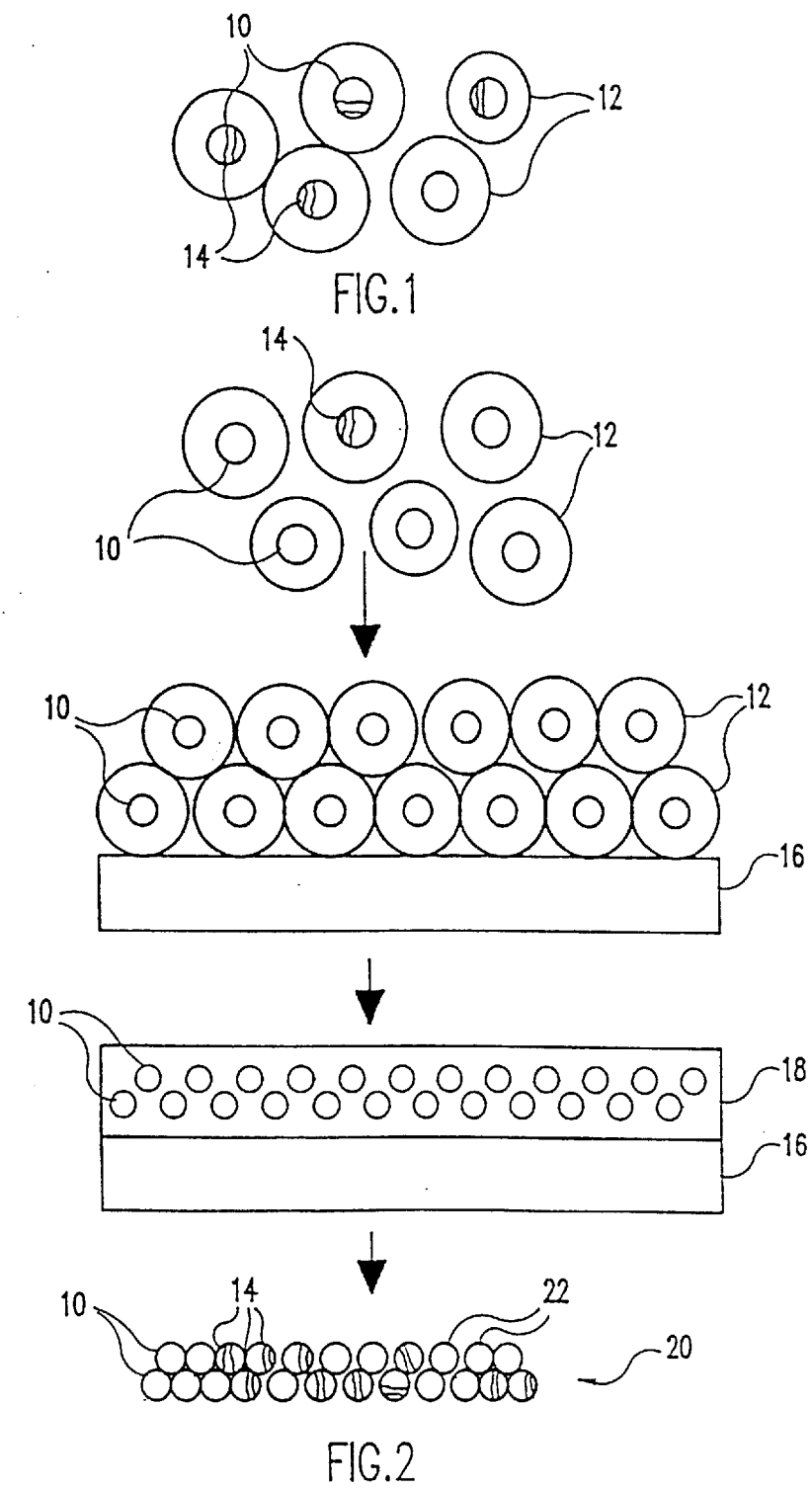

UV ABSORBING GLASS

CROSS-REFERENCE TO RELATED APPLICATIONS

This application is a divisional of application U.S. Ser. No. 08/261,900, filed Jun. 15, 1994, now abandoned which is a CIP of U.S. Ser. No. 07/991,130, filed Dec. 16, 1992, abandoned, which are hereby incorporated herein by reference.

DESCRIPTION

BACKGROUND OF THE INVENTION

1. Field of the Invention

The invention generally relates to metal oxide particles, the method of manufacturing the same, and their use in a variety of applications and compositions, and more particularly to UV absorbing glass containing such particles and a method for preparation of the UV absorbing glass.

2. Background of the Invention

U.S. Pat. No. 5,077,133 to Cheng describes the use of ceric oxides, iron oxides, and titanium oxides in the production of glass compositions which transmit visible light and block UV light and IR light. The Cheng process contemplates starting with a composition containing a cerium source compound such as cerium carbonate, melting the composition together to form a green glass, and then casting the green glass onto a molten metal bath in a float glass process.

U.S. Pat. No. 4,027,073 to Clark discloses the use of colloidal silica and $CH_3Si(OCH)_3$ monomer which upon hydrolysis followed by heat cure is said to give abrasion resistant coatings for polycarbonate. In this patent organic ultraviolet absorbers such as benzophenones were used to prevent the penetration of ultraviolet (UV) light from reaching the polycarbonate surface and hence prevent UV-initiated degradation. However, the organic UV blockers age with time due to oxidation and lose their UV blocking properties. In U.S. Pat. No. 4,275,118 to Baney et al. the organic UV blockers were replaced with colloidal titania as a UV blocking agent and the rest of the recipe was similar to that of Clark.

In U.S. Pat. No. 4,799,963 to Basil et al. ultraviolet barrier coatings were made for polycarbonate using colloidal cerium oxide to obtain metal oxide-ceria, preferably silicon oxide-ceria composite coatings. In these coatings, the matrix forming components were the organo-alkoxide monomers with the general formula $R_xM(OR')_{z-x}$ which on hydrolysis and condensation at elevated temperatures formed a glassy network matrix in situ. Here, R and R' were organic radicals, M was selected from the group consisting of silicon, aluminum, titanium, zirconium and mixtures of thereof, z was the valence of the metal and x was less than z. U.S. Pat. No. 5,035,745 to Lin et al. also discloses the use of the alkoxide, monomers $R_xM(OR')_{z-x}$ to obtain an in situ coating matrix. The entire solution is passed through an ion exchange resin to remove sodium ions. U.S. Pat. No. 5,344,712 to Basil et al. mentions the use of small quantities of polyvinylpyrrolidone as an additive to improve the adhesion properties of the coating. Here too the alkoxysilane monomers were utilized to obtain a glassy matrix. In addition to the use of metal alkoxides, all of these formulations involved the use of colloidal silica and silica forming compounds such as methyltrimethoxysilane $CH_3Si(OCH3)_3$, and tetraethylorthosilicate (TEOS) to give silane-ceria composite coatings. Also, these formulations required the addition of organic solvents such as isopropanol, ethanol, methanol, butanol etc., in the coating compositions. These alcohols were also generated in situ by the hydrolysis of their respective alkoxide precursors. That made the coating compositions potentially flammable and environmentally hazardous. The coating compositions in the above mentioned patents were designed for rigid polycarbonate substrates due to the glassy matrix they yielded. Due to their rigidity these coatings were not suitable for flexible substrates such as thin plastic window films.

U.S. Pat. No. 5,066,248 to Anderson et al. describes the formation of metal oxide ceramic membranes of small pore size by a sol-gel process. Metal alkoxides having an alkoxyl group of branched structure and at least four carbon atoms are dissolved in an alcohol solution with a very limited amount of water. By slowly evaporating the water and alcohol and firing the gel produced therefrom, a particulate metal oxide ceramic membrane is produced. Anderson et al. explains that using a large alcohol group in the metal alkoxide precursor facilitates the creation of very small particles in the sol stage. Anderson et al. suggests adding polymeric stabilizing agents such as polyethylene glycol and hydroxypropyl cellulose at various stages of the particle growth process to quench particle growth at a size of interest (e.g., 2–300 nm). The Anderson et al. process has the drawbacks of requiring a time consuming transesterification step and the addition of acid to control the reaction rate.

Jean et al., *Mat. Res. Soc., Symp. Proc.,* 73:85 (1986) and Jean et al., *Colloids and Surfaces,* 29:273 (1988) discuss a chemical synthesis wherein hydroxypropylcellulose (HPC) adsorbs onto the surfaces of titanium dioxide particles as they are formed. HPC generates repulsive steric forces that limit particle aggregation and result in spherical articles with a relatively narrow size distribution. Particle sizes of the titanium dioxide particles are reduced by including increasing quantities of HPC; however, once above a critical HPC concentration that corresponds to nearly complete surface coverage of HPC, a plateau on particle size is reached. The titania particles produced according to the Jean et al. techniques have an average size of 300 nanometers. Jean et al. did not recognize the role played by water concentration in the formation of smaller diameter titania particles and only used water molar concentrations equal to or slightly greater than the metal alkoxide (e.g., the ratio of moles of water to moles of titanium ethoxide never was greater than 5 or 10).

It would be advantageous to provide a more simplified method for producing metal oxide particles. In addition, a method of producing smaller particles would be beneficial since smaller particles have more versatility than larger particles and will be more transparent to visible light.

It would be advantageous to provide a low cost, low temperature process for manufacturing ceramic particles and films that does not require the use of sophisticated equipment and which would be useful in a wide variety of applications.

It would also be desirable to provide a process for protecting an article against UV radiation by incorporating a visible light transparent, UV blocking metal oxide particles into at least a surface of the article to be protected.

SUMMARY OF THE INVENTION

The present invention is directed to the use of small particles of metal oxide to protest an article from ultraviolet (UV) radiation. By using small particles less than 200 nm, preferably less than 70 nm, the particles can be deposited into the substrate or on a surface of the substrate in the form of a transparent film or coating. By using metal oxide particles such as cerium oxide, titanium oxide and the like, for example, the particles will block ultraviolet radiation. By having a sufficiently high concentration of the particles in the article or the film or coating on a surface of the article, and a sufficient thickness of the film or coating, the article can be essentially protected from incident UV radiation while preserving the optical qualities of the substrate and/or substrate surface since the film metal oxide particles is transparent.

The present invention is more particularly directed to a simple method to make UV barrier coatings using cerium oxide sol, preferably in water. It involves, in one aspect, the use of water based or water soluble polymers such as polyvinyl alcohol and hydroxypropylcellulose as the ingredient to form a polymer matrix in which the colloidal oxide particles are dispersed. Waterborne polymers such as silanol terminated polydimethylsiloxane can also be used to obtain flexible coatings. These coatings are well suited for coating both article surfaces, as well as granules or other starting materials used to make bulk materials. Coatings are water based and hence environmentally attractive.

Powders or granulated materials are coated to encapsulate or distribute the oxide particles within the bulk of the material and thus make articles made from the bulk materials a barrier to ultraviolet light. For instance, purified sand, an essential ingredient to make float glass, is coated with aqueous cerium oxide solution, optionally containing a water soluble polymer as a binder, and dried. The coated sand is then mixed with other ingredients and fired conventionally to obtain transparent UV barrier glass which has a sharper UV cutoff and appears less yellow than the prior art glasses containing the same amount of cerium. Similarly, plastic powders or pellets are coated with oxide solution and extruded to form transparent UV barrier plastic sheets or films.

Flat and other geometrically configured surfaces are coated to minimize the penetration of ultraviolet rays and protect the surface underneath from ultraviolet degradation. Coatings are made on flat flexible surfaces such as plastic window films and textile products. Flat rigid surfaces include wood, glass, plastic sheets such as polycarbonate, acrylics, etc.

The present invention does not involve the use of metal alkoxides to form in situ polymers with the evolution of alcohols. Coatings are water based and hence environmentally attractive. Coatings can be applied utilizing common coating techniques such as dip, spray, spin, flow, rod, etc. The coating composition can also contain small amounts of wetting and curing agents which promote adhesion. Curing agents such as melamine formaldehyde (MF) resin, hydrogen terminated silanes, methyltrimethoxysilane, tetramethoxysilane, tetraethoxysilane and the like are used to crosslink the polymer matrix to get a durable and water resistant coating. The coating hardness increases with the concentration of the curing agent. For instance, 5 weight percent polymer and 95 weight percent (weight based on polymer concentration) melamine formaldehyde in the coating compositions gives a hard abrasion resistant UV barrier transparent film.

In one aspect, the present invention provides a method for protecting a substrate from exposure to UV radiation. The method includes the steps of applying a dispersion of UV-blocking metal oxide particles to a surface of the substrate, and drying the applied dispersion to form an essentially transparent film on the substrate surface. The dispersion is preferably in the form of an aqueous polymer solution, and the polymer is present in the dispersion in an amount of at least 5 percent by weight of the metal oxide particles. The metal oxide particles have a particle size distribution substantially less than 200 nm, preferably less than 70 nm. The transparent film formed on the substrate surface is in the form of metal oxide particles distributed in a matrix of the polymer.

The transparent film preferably contains a sufficient concentration of the metal oxide particles, and has a thickness effective to block at least 50 percent of UV radiation at wavelengths less than 360 nm. The dispersion preferably contains from 1 to 30 percent solids, and preferably up to 10 percent by weight of the metal oxide particles. The metal oxide particles are preferably cerium oxide. The application of the dispersion to the substrate surface can be effected by spraying, dipping, brush coating, metering rod coating, rigid knife coating, flexible knife coating, roll applicator coating, cast coating, pre-cast coating, curtain coating, or the like. The drying step can be effected using a direct-heat dryer, indirect-heat dryer, radiant-heat dryer, dielectric dryer, or the like.

The substrate surface is preferably wood, glass, plastic, textile, paint or the like.

The polymer is preferably polyvinyl alcohol, hydroxyalkylcellulose such as hydroxypropylcellulose or hydroxyethycellulose, polyalkylene oxide such as polyethylene glycol or polypropylene glycol, or the like. The dispersion can also include a water repellent, such as silicone or fluoropolymer, for example.

In another aspect, the present invention provides a method for protecting a substrate from exposure to UV radiation. The method includes applying cerium oxide particles smaller than 200 nm, preferably smaller than 70 nm in an aqueous dispersion containing a water soluble polymer to a surface of the substrate; drying the applied dispersion to form an essentially transparent film on the substrate surface of the cerium oxide particles distributed in a matrix of the polymer having a thickness and concentration of the cerium oxide particles effective to block at least 80 percent of radiation at wavelengths between 200 and 400 nm; and exposing the substrate surface to UV radiation, whereby the transparent film substantially blocks the UV radiation to protect the substrate. The dispersion preferably contains from 1 to 30 percent solids and has a weight ratio of the cerium oxide particles to the polymer from 5:95 to 95:5. The dispersion preferably contains up to 10 weight percent cerium oxide particles. The substrate surface is preferably wood, glass, plastic, textile, paint, or the like. When the substrate surface is wood, the dispersion preferably also includes a silicone water repellent. The polymer is preferably hydroxyalkocellulose or a polyalkylene oxide.

In a further aspect, the invention provides a method for protecting the article from exposure to UV radiation. The method includes forming a film of metal oxide particles on a surface of the article, wherein the film is essentially transparent to visible light and substantially blocks ultraviolet radiation. The film preferably includes a film-forming polymer with the metal oxide particles dispersed therein. The metal oxide is preferably cerium oxide. The metal oxide particles preferably have a size distribution substantially between 10 and 200 nm, more preferably between 10 and 70 nm, and particularly up to 20 nm. The article is preferably a substrate selected from plastic, wood, textiles, glass, paint, and the like. The method of protecting preferably includes the further step of exposing the article to ultraviolet radiation wherein the surface of the article is protected from the ultraviolet radiation by the film formed thereon.

BRIEF DESCRIPTION OF THE DRAWINGS

The invention, will be better understood from the following detailed description of the preferred embodiments of the invention with reference to the drawings, in which:

FIG. 1 is a stylized depiction of a plurality of porous metal oxide particles with adsorbed polymer on the surfaces of the metal oxide particles;

FIG. 2 is a schematic diagram showing a process for producing both polymeric and ceramic films with the porous metal oxide particles with adsorbed polymer on the surfaces shown in FIG. 1;

DETAILED DESCRIPTION OF THE INVENTION

Figure 3:
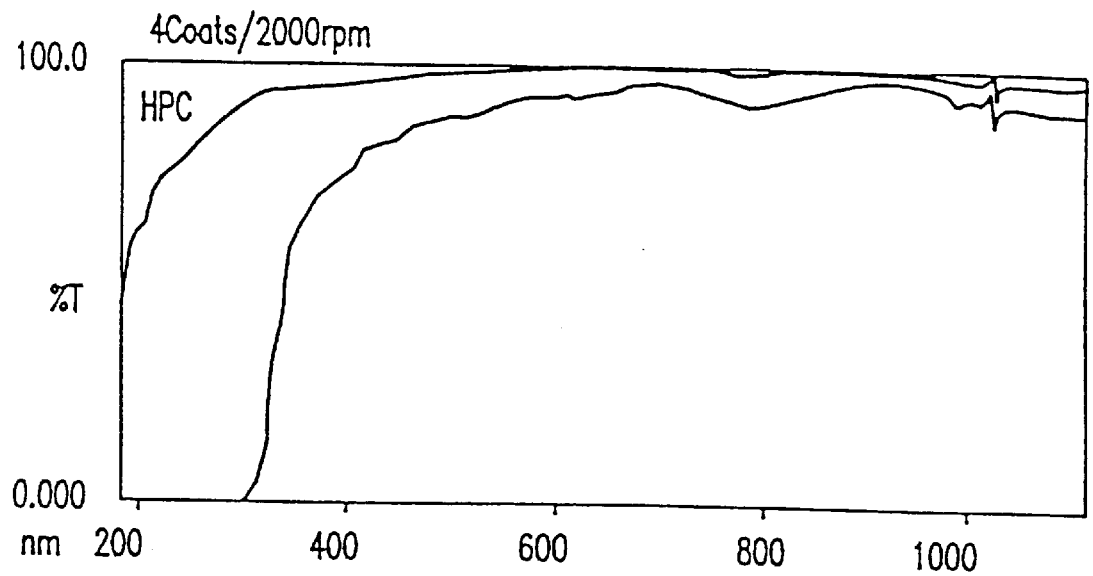
FIG. 3 is a graph showing the UV/Vis transmission characteristics of a $TiO_2$/HPC thin film on quartz.

Porous metal oxide particles according to the present invention are prepared via chemical synthesis wherein a metal alkoxide precursor is dissolved in a suitable solvent and is hydrolyzed by water in the presence of a dissolved, steric stabilizing polymer and then condensed to form the metal oxide of interest. Reaction schemes 1 and 2 provide simplified reaction steps for a large number of metal alkoxides, i.e., titanium alkoxide, etc.

Scheme 1

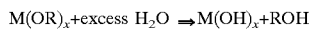

Scheme 2

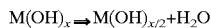

The metal oxides which can be produced according to this synthesis are wide ranging and particularly include cerium oxides, zirconium oxides, niobium oxides, tantalum oxides, titanium oxides, indium oxides, aluminum oxides, and tin oxides. Although not mentioned, other metal oxides and metal oxide blends (e.g., indium-tin oxide) may also be prepared according to the present invention. In addition, mixtures of two or more metal alkoxides as starting materials could be utilized to produce composite particles of two different metal oxides. This would be particularly important, for example, if a ceramic or polymerceramic film having both infrared and UV barrier properties were to be prepared. Specifically, tin oxide, indium oxide, or doped indium-tin oxide (ITO) are useful as infrared (IR) barriers, while titanium oxides and particularly cerium oxides are useful as ultraviolet (UV) barriers. The alkoxides of the metal alkoxide precursors can vary widely, and particularly include methoxides, ethoxides, isopropoxides, butoxides, methoxyethoxides, ethoxymethoxides, and ethoxyethoxides. However, it should be understood that other alkoxides may be useful within the practice of the present invention.

The solvent system for the metal alkoxide precursors can be methanol, ethanol, propyl alcohol, isopropyl alcohol, butyl alcohol, secbutyl alcohol, tertbutyl alcohol, tetrahydrofuran, water, methoxyethanol, and pyridine. Other solvents may also be useful in the practice of the invention, as well as combinations of two or more different solvents.

The steric stabilizing polymer is believed to play a critical role in the synthesis process of adsorbing onto the surface of the titanium oxide as it is formed. In order for the reaction to proceed properly, the steric stabilizing polymer must remain in solution until the metal oxides condense. Subsequent to condensation, the steric stabilizing polymer adheres to the surface of the metal oxides and ultimately prevents the continued growth of metal oxide particles. In general, polymers having hydroxy groups or carbonyl groups can provide steric stabilization via interactions such as hydrogen bonding and would be suitable for practicing the present invention. Suitable steric stabilizing polymers include hydroxypropyl cellulose as well as other hydroxyalkyl substituted cellulose products, hydroxy functionalized polypropylene oxides, polyethylene glycols, etc. The steric stabilizing polymer should be soluble in a solvent system comprising water and an organic solvent through hydrogen bonding. Furthermore, the hydroxy functional groups also provide the site for adsorption onto metal oxide surfaces via hydrogen bonding. The molecular weight of the steric stabilizing polymer should range between 2 kg/mole and 5,000 kg/mole.

When preparing the porous titanium oxide particles, the concentration of the steric stabilizing polymer dissolved in solution should be greater than 0.1 g of polymer per liter of solution. The combined solution of the metal alkoxide and the steric stabilizing polymer should include, in the dry film form, 5–95% by weight of the metal alkoxide and 5–95% by weight of the steric stabilizing polymer, and is most preferably on the order of 40–60% of the metal alkoxide by weight and 40–60% of the metal alkoxide by weight and 40–60% by weight of the steric stabilizing polymer, in the dry film form. The metal alkoxide and steric stabilizing polymer will be combined in water and the solvent system. A critical parameter for producing small particles on the order of 200 nm or less is the molar ratio of water to the metal alkoxide precursor in the solution. Equation 1 shows that the molar ratio R must be at least fifteen and is more preferably substantially greater than fifteen (e.g., R=30–200) Eq. 1

$$R = [H_2O]/[M(OR)_x] \geq 15$$

Experiments have demonstrated that there is a reduction in particle size with increased water concentration. This effect may be explained by the kinetics of the hydrolysis and condensation reactions, the adsorption of the steric stabilizing polymer on the metal oxide, and the solubility of the steric stabilizing polymer in the reaction medium.

As discussed below in Example 1, experiments wherein titania was produced from a solution of tetraethylorthotitanate (TEOT) and hydroxypropylcellulose (HPC) in ethanol and water have shown that the particle diameter of titania decreases nearly five fold as the ratio of water to TEOT increases from 5.3 to 60. At R=60, particles on the order of 70 nm were obtained. In addition, the mass of adsorbed steric stabilizing polymer HPC on the titania metal oxide particle increases by more than three-fold as the ratio of moles of water to moles of TEOT, R, increases from 5.3 to 60. This may be the result of water being preferentially adsorbed via formation of a more polar and stronger hydrogen bond with Ti-OH sites than does ethanol. The adsorbed water may enhance HPC adsorption through the formation of hydrogen bonds between the Ti-OH surface sites and the hydroxyl groups on the HPC. Ethanol cannot participate in a hydrogen bond bridge between a Ti-OH surface and an HPC chain.

FIG. 1 is a stylized depiction of a plurality of titanium oxide particles 10 centrally disposed within a plurality of adsorbed polymer spheres 12. As the chemical synthesis of the metal oxides proceeds, metal oxide particles 10 with adsorbed steric stabilizing polymers begin to fall out of solution. FIG. 1 shows that the spherical titanium oxide particles 10 of the prevent invention are porous, and the channels 14 extend in and through the metal oxide particles. However, it should be understood that the channels 14 shown in FIG. 1 are much larger on a relative scale to the metal oxide particle 10 than is actually achieved, and that FIG. 1 is simply intended to show that the particles are porous, not the actual configuration of the porous particles. The channels 14 are created during particle formation.

The porous titanium oxide particles 10 can be collected by burning off the adsorbed polymer spheres 12 from the surfaces, by dissolving the polymer spheres 12, or by other suitable means. Burning off the polymer is the preferred technique. When HPC is used as the steric stabilizing polymer, the porous metal oxide particles can be collected by heating at 250° C. A significant advantage of the porous metal oxide particles of the present invention is their size. Due to the use of excess water in the fabrication process, the size of the particles can be on the order of 10–200 nm in diameter. At this size, and due to the porous character of the particles, the particles are virtually transparent to visible light. This is because the diameter of the particle is smaller than the wavelengths of visible light which range between 380 nm to 760 nm.

Metal oxide particles can be used in many applications. For example, metal oxide particles prepared according to the above-described procedure, or prepared by a different procedure but having about the same particle size distribution, can be used to make products with UV and IR barrier properties. In particular, the metal oxide particles can be combined with a cleaning agent, for example, such as a glass cleaner, car polish, vinyl protectants, furniture polish, shoe polish, etc., at an amount of less than 5–10% by weight, and most preferably at an amount of less than 1% by weight of the final composition. The metal oxide particles can be included in the cleaning agent with or without the adsorbed steric stabilizing polymer, or another binding agent to facilitate retaining the metal oxide particles on a surface to which the cleaning agent has been applied. The cleaning agent is applied to the substrate to be protected in its normal fashion. The porous particles of the present invention remain on the substrate and allow transmission of visible light, but provide a barrier to UV and/or IR light depending on the metal oxide particles utilized. Tin oxide, indium oxide, or doped indium-tin oxide (ITO), for example, are useful as infrared (IR) barriers, while cerium oxides and titanium oxides are useful as ultraviolet (UV) barriers. UV light is responsible for the deterioration of a wide variety of products including leather goods, polymeric materials, etc. Hence, providing a UV barrier prolongs the life of these products. Blocking IR light has the advantage of minimizing the total light energy, and attendant heat, to which a product is exposed.

In addition, the metal oxide particles might be included in cosmetic products such as lipstick, suntan lotion, bug repellent, shampoo, etc. Ideally, the metal oxide particles constitute less than 5–10% by weight of the cosmetic product, and most preferably less than 1% by weight. As with cleaning agents, the metal oxide particles are provided in the cosmetic product with or without the adsorbed steric stabilizing polymer, or other binders. The advantage of using HPC or other cellulose derivatives as the steric stabilizing polymer is that the substance functions as a binder for the metal oxide particles and is not a hazard to humans or animals. The cosmetic product is applied according to normal practice, and the metal oxide particles left behind provide protection to the user's lips, hair, skin, etc. In the bug spray application, the user receives protection from both insects and UV exposure.

The porosity of the titanium oxide particles may provide advantages in cosmetic and pharmaceutical applications. For example, perfume can be positioned in the pores of the metal oxide particles. This is achieved by combining the particles with the perfume for a period of time sufficient for the perfume to penetrate into the pores. Pressure can be used to enhance penetration of the perfume into the pores. After the cosmetic product, e.g., eye shadow, blush, etc., which contains the metal oxide particles is applied, the perfume is slowly released over time from the pores of the particles. Alternatively, a drug may be positioned in the particles and the particles are provided to a patient as part of an implant or wound dressing. The drug is delivered over time to the patient from the pores of the particles.

The metal oxide particles may also be sprayed onto a substrate such as glass to provide a UV and/or IR barrier. In addition, the metal oxide particles may be combined with glass-forming substances during the fabrication of the glass, for example, 0.3 to 2 weight percent $CeO_2$ coated on sand particles used to make float glass.

FIG. 2 shows the titanium oxide particles 10 with a binder 12 being cast on a substrate surface 16 such as glass, ceramic, wood, plastic, textile, paint, composite, etc., by a suitable means for distributing the particles 12 such as spraying, dipping, brush coating, metering rod coating, rigid knife coating, flexible knife coating, roll applicator coating, cast coating, pre-cast coating, curtain coating, etc. The polymer 12, which can be the steric stabilizing polymer used in the manufacture of the metal oxide particles, or another binder mixed with the oxide particles, is subsequently dried by application of heat or by other means such as, for example, by using a direct-heat dryer, indirect-heat dryer, radiant-heat dryer, dielectric dryer, or the like. This produces a film 18 with evenly distributed metal oxide particles 10 in a matrix of the polymer 12. The polymer 12 (or wax or other binder) assists in obtaining an even or uniform distribution of the metal oxide particles 10 by physically spacing the particles from each other via the thickness, concentration, and molecular weight of the polymer 12. If HPC is used in the fabrication of the film 18, the drying temperature should be low (e.g., on the order of 150° C.). The film may be subsequently cured using a suitable film curing agent such as citric acid to make the film more solvent resistant.

Multilayer films can be made easily since the polymers and/or binders in adjacent layers can be compatible. By controlling each layer's composition, the layer's refractive index can be controlled, resulting in films with preferred refractive index gradients. For example, narrow band pass filters which pass light at only selected wavelengths can be fabricated by casting films having different metal oxide particle concentrations and thicknesses on top of one another. Preferably, multiple layers are spin coated or dip coated in a "sandwich" structure that results in a controlled refractive index.

FIG. 3 shows the percent transmission versus wavelength curves for a titania/HPC film created from a solution/suspension of 48% by weight titania ethoxide and 52% by weight HPC where the film was created from four successive layers of metal oxide particles coated with adsorbed HPC being cast on a quartz substrate by spin coating each layer at 2,000 rpms. The data in FIG. 3 show that pure HPC film is transparent to UV light, whereas the film containing the porous titania particles essentially blocks UV radiation below 320 nm, but is essentially transparent to visible light, transmitting more than 95% of the light in the visible region. The total impermeability of UV radiation bellow 320 nm results from the titania particles strongly absorbing UV radiation at these shorter wavelengths. The use of similarly sized cerium oxide particles essentially blocks UV radiation below about 360 nm. As discussed above, different metal oxide particles can be used in the films. For example, indium oxide, indium-tin oxide, and tin oxide particles, which absorb IR radiation, can be used to fabricate an IR barrier. In addition, metal oxide particles, such as cerium oxides, may be combined with titanium oxide particles, to block more of the UV spectrum.

Films may also be made using conventional extrusion processes wherein the metal oxide particles are either combined with a polymeric material or binder, or are provided together with adsorbed steric stabilizing polymer, and are extruded through a die to produce a film with porous metal oxide particles dispersed in the polymer or other binder. The films can be used to protect packaged equipment, food products, etc., from damaging UV or IR light.

In addition to providing a barrier to certain wavelengths of light, polymer films which include the metal oxide particles will have reduced fluid and gas permeability due to the densification provided by the particles. As discussed above, curing agents can be added to enhance resistance to fluid or gas permeability. It should also be understood that the metal oxide particles can be harvested from the adsorbed steric stabilizing polymer, and combined with a high temperature thermoplastic or thermosetting polymer such as polyamides or polyimides.

FIG. 2 also shows that ceramic films can be prepared from the porous metal oxide particles. In particular, after casting the particles with adsorbed steric stabilizing polymer, the steric stabilizing polymer is burned off leaving a ceramic film. In the case of HPC being used as the steric stabilizing polymer, the polymer can be burned off at 250° C. The porosity, crystalline state, and size of particles in the film can be changed by sintering at different temperatures. In general, the refractive index of the particles increases with increasing temperature and the porosity decreases with increasing temperature.

In a specific example, the titania particles produced according to Example 1 will remain amorphous until heated to a temperature above 500° C. whereupon they begin to transform to anatase crystal form. Annealing above 600° C. results in a transition from anatase to rutile. The ceramic film will remain transparent to visible light when sintered or annealed up to temperatures of 700° C.; however, the films will become increasingly opaque as the temperature increases above 700° C.

It is anticipated that the ceramic films of the present invention will be post film formation heat treated at temperatures ranging between 200° C. and 2000° C. FIG. 2 shows the ceramic films 20 will have pores 22 between adjacent metal oxide particles 10, as well as pores 14 through the metal oxide particles themselves since the fabrication technique for producing the particles results in porous metal oxide particles. The ceramic films have a wide variety of uses. For example, due to the thermal stability of the ceramic films, they may be used as filters for high temperature gases and molten ores. In addition, the ceramic films can serve as catalyst supports. The films may also be used as protective coatings or abrasion resistant coatings. In a particular application, the films may be coated on light fixtures or light bulbs which produce UV light or IR light to block the same (e.g., incandescent bulbs produce UV light).

The thickness of the ceramic film 20 is controlled by controlling the size of the metal oxide particles produced during the synthesis process and controlling the number of layers with metal oxide particles having adsorbed polymer thereon that are made prior to sintering away the steric stabilizing polymer. The thickness can also be controlled by controlling the polymer concentration and molecular weight.

EXAMPLE 1

Materials and Methods

Tetraethylorthotitanate (95 wt % TOET, 5% ethanol) was obtained from Alfa Chemical Company. Anhydrous ethanol (200 proof) was obtained from the Aaper Alcohol and Chemical Company. Hydropropylcellulose (HPC) was obtained from Hercules Incorporated. The structure of HPC comprises a cellulose backbone with hydroxpropyl groups substituted at the anhydroglucose units. The hydroxypropyl groups make HPC soluble in water and alcohols (e.g., EtOH) via hydrogen bonding. HPC is also adsorbed on surfaces by hydrogen bonding groups. The nominal molecular weights used in the study were 60 kg/mole and 1150 kg/mole. For purposes of this study the 60 kg/mole HPC is designated HPC E, and the 1150 kg/mole HPC is designated HPC H. The molecular weight of the HPC polymer was analyzed with a gel permeation chromatograph equipped with an intrinsic viscosity detector that measures absolute molecular weight distribution. The resulting molecular weights for HPC E were $M_n$=40 kg/mole and $M_w$=68.5 kg/mole. The HPC H sample formed gel particles in the mobile phase and could not be analyzed accurately. The HPC samples were dried in a vacuum oven prior to ther used in $TiO_2$ particle growth experiments. Deionized water with a resistivity of $16-18\times10^6$ ohm-cm was used in all of the experiments. Hydrogen peroxide and sulfuric acid were obtained from Fisher Scientific and were used for spectrophotometric assays for HPC and soluble titanium species. Glassware was cleaned thoroughly before use.

For particle synthesis, equal volumes of solutions of TEOT in ethanol were mixed with solutions of HPC in ethanol and water. All solutions were filtered before mixing through a 0.2 micron filter. The TEOT solutions were handled in a nitrogen glove bag to prevent premature hydrolysis of the ethoxide. The water concentrations in these experiments varied over the range of $5.3 \leq R \leq 60$ and the TEOT concentration was 0.075M. Since the experiments, particles have been synthesized where the R value was in excess of 100. The extent of conversion of the TEOT after 20 hours was determined by a spectrophotometric method.

The effect of solvent composition on the hydrodynamic diameter of HPC was measured to determine how the solvent composition affected the solubility of HPC. The hydrodynamic diameter, $D_h$, was measured with a variable angle dynamic light scattering correlator equipped with an argon ion laser operated at a wavelength of 514.5 nm. Measurements were made at a scattering angle of 90° and a temperature of 25±1° C. The hydrodynamic diameters were calculated using the second cumulants method.

Mean $TiO_2$ particle sizes were determined 24 hours after mixing by transmission electron microscopy (TEM). Particle sizes were determined by counting at least 100 particles to obtain a mean number particle diameter as well as a standard deviation of the particle size distribution.

The effect of water concentration on the adsorption of HPC with $TiO_2$ was characterized using the Karl-Fischer titration method by measuring the adsorption of water on previously made $TiO_2$ in ethanol. All adsorption experiments were performed with $TiO_2$ particles synthesized in the absence of HPC at R=5.3. Prior to these experiments, the particles were washed thoroughly with anhydrous ethanol and were sonicated but were never dried.

The effect of water concentration on the polymer adsorption was studied at two extreme concentrations of the polymer, $C_p$=0.24 g/l and $C_p$=1.7 g/l, which concentrations corresponded to partial and nearly complete coverage of $TiO_2$ particles as determined from the particle growth experiments. The mixtures were agitated at room temperature for 24 hours followed by centrifugation. The concentration of HPC in solution was measured spectrophotometrically with a standard colorimetry assay. At least three replicates were made for each point on the absorption isotherm curves.

$TiO_2$ suspensions in initially anhydrous ethanol were equilibrated with various concentrations of water. After agitation for 24 hours followed by centrifugation, the supernatant was removed and analyzed for water concentration. At least three replicates were made for each sample and care was taken to prevent contamination by atmospheric moisture.

Results of Water Concentration on Particle Size

Figure 4:
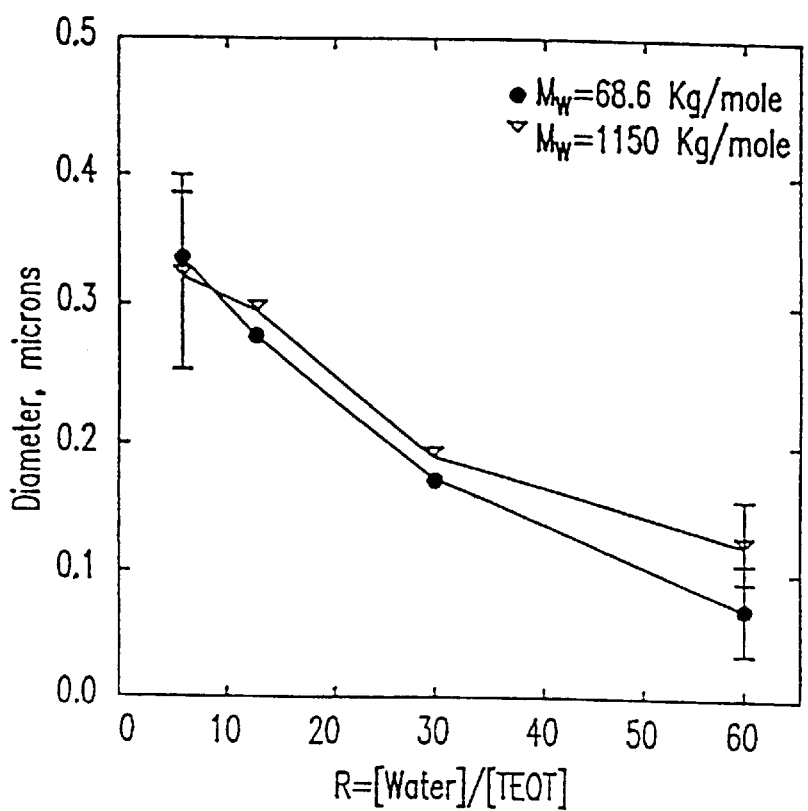
FIG. 4 is a graph showing the effect of water concentration on metal oxide particle diameter.

FIG. 4 shows there was a marked reduction in mean particle diameter with increasing water concentration from 5.3 to 60 for HPC E and HPC H at an HPC concentration $C_p$=1.7 g/l. For HPC E, there was a nearly five-fold reduction in particle size, reaching a minimum value of 70 nm. Experiments with HPC H ($M_w \approx$ 1150 kg/mol) showed sizes nearly indistinguishable from those grown with HPC E at low R values. By contrast, particles grown without HPC were irregular aggregates of approximately 2–10 µm in size. At R=60, the relative standard deviation for particles grown with HPC E decreased from 60% to 43% as the HPC concentration increased from 0.42 g/l to 1.7 g/l. The extent of conversion after 24 hours increased with water concentration, rising from 35% at R=5.3 to over 99% for R≧30 and was independent of HPC.

The reduction in particle size with water concentration in the reaction mixture at a fixed polymer and TEOT concentration may be due to the effect of water concentration on the kinetics of hydrolysis and condensation reactions.

Hydrolysis 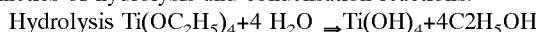

Condensation 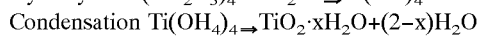

In addition, the adsorption of HPC on $TiO_2$ and the solubility of HPC in the reaction medium play a role. Specifically, the mass of HPC/g $TiO_2$, $\Gamma_{HPC}$, increased by three-fold as the water mole fraction $X_W$ increased from 0.01 (R=5.3) to 0.12 (R=60) at a fixed HPC molecular weight and concentration. In addition, the adsorbed amount $\Gamma_{HPC}$, increased with HPC molecular weight since the longer chains have more segments to adsorb onto the $TiO_2$. It was also determined that water preferentially adsorbed on $TiO_2$ in ethanol.

The effect of water concentration on the solubility of HPC in the reaction medium is important as this can affect the adsorbed amount $\Gamma_{HPC}$, and the thickness of the adsorbed layer on $TiO_2$. Table 1 shows the hydrodynamic diameter, $D_h$, for HPC H in a mixture of ethanol and water.

TABLE 1

| Mole Fraction Water, $X_w$ | $D_h$, nm |
|---|---|
| 0.0 | 70 |
| 0.01 (R = 5.3) | 72 |
| 0.12 (R = 60) | 78 |
| 1.00 | 210 |

The hydrodynamic diameter for HPC in a mixture of ethanol and water increased by approximately 7% over the range of water concentration 5.3≦R≦60. This shows that HPC is somewhat more soluble in water than in ethanol.

The experiments show that an increase in water concentration at fixed HPC concentration leads to smaller particle size due to the combined effects of increased HPC adsorption and nucleation rates. This latter point was evidenced by the time required for the onset of turbidity. For R=5.3 at all HPC concentrations, the typical time required for reaction mixtures to become turbid after the addition of water was greater than 10 minutes. By contrast, where R≧30, the mixtures became turbid within five seconds.

EXAMPLE 2

Titania particles were prepared as described above in Example 1; however, the ratio of moles of water to moles of TEOT, R, was 120. A suspension of titania/HPC particles, at 4 wt % solids (48% $TiO_2$), was combined with a variety of cleaning agent products at 1–2 gm of the titania/HPC suspension and 1 gm of the product to produce a composition having approximately 1–1.5 wt % titania particles. The products tested were as follows:

1. STP protectant (spray)—used for vinyl protection in car interior.
2. Armorall (spray)—used for vinyl protection in car interior.
3. Glass-Plus (spray)—glass and window cleaner.
4. Old English Furniture Polish (spray).
5. Turtle Wax Furniture Polish (spray).
6. Turtle Wax Car wax (wax).
7. Nu Finish Car Polish (thick suspension).

Figure 5:
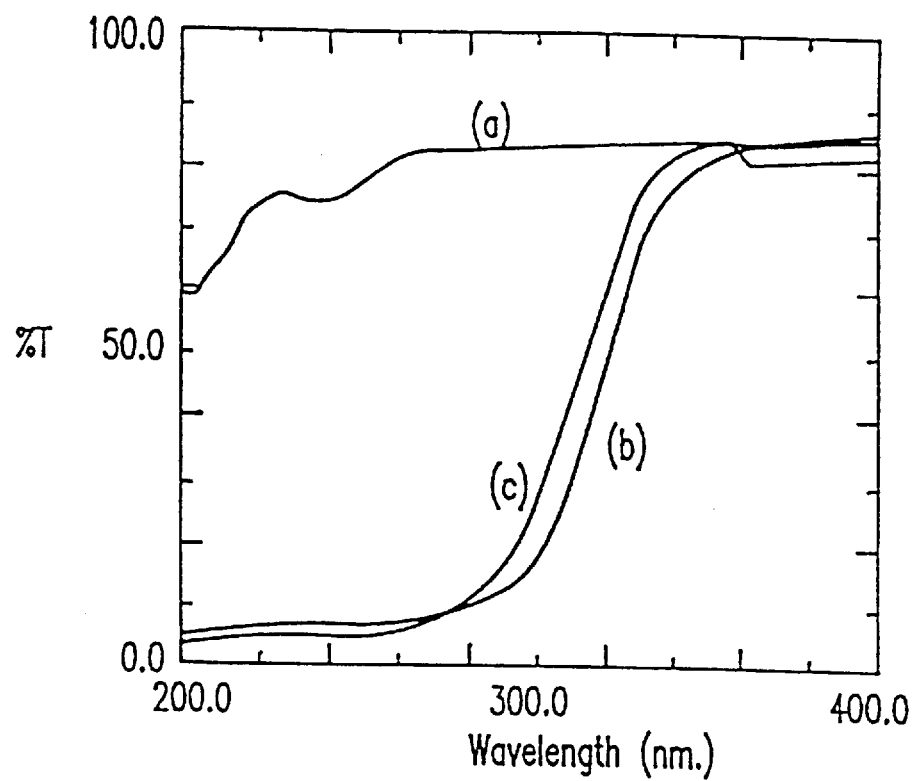
FIG. 5 is a graph showing the UV/Vis transmission characteristics of a composition including a cleaning agent and $TIO_2$/HPC.

For each type of product, the combination titania/HPC and cleaning agent were applied to a quartz wafer and the UV/Vis spectrum was scanned from 2,000 to 200 nm. For comparison purposes, the cleaning agent alone was applied to similar quartz wafers and the UV/Vis spectrum. The spectra showed that none of the products tested provided any barrier to UV light. That is, the spectra were flat for the entire range scanned. By contrast, the combination of titania/HPC and cleaning agent provided a barrier of UV light below 300 nm. FIG. 5 is exemplary of the test results and shows the following spectra: (a) the Glass-Plus glass cleaner alone, (b) the glass cleaner and HPC/titania combination wherein the combination was applied then blown dry, and (c) the glass cleaner and HPC/titania combination wherein the combination was applied then wiped dry in a circular motion. FIG. 5 shows the combination of the cleaning agent and HPC/titania was effective when rubbed dry as is normally done by the consumer.

EXAMPLE 3

One gram of 20% ceria sol in water (10–20 nm; pH 1.5–3.0) was mixed with 2 g of 6 wt % polyvinyl alcohol (PVA) (AIR Products) in water and shaken vigorously. To this solution 0.06 g of 40 wt % melamine-formaldehyde (MF) resin (Cytech Industries) in water was added as a curing agent to crosslink the PVA polymer. Heat curing of PVA with MF was catalyzed by adding 0.02 g of 1 wt % para-toluenesulfonic acid catalyst.

The mixture was shaken vigorously and was allowed to stand for 10 minutes for the foam to settle. Defoaming agent can be added to expedite this process. Also, a biocide can be added to prevent the biological degradation of PVA. The above solution was used to coat transparent polyethylene terephthalate (PET) film. The coating was done by placing the film on a thick glass sheet and hand drawing the solution using a wire cator (BYK-GARDNER part # AR 4122). A clear coat was obtained which was dried and cured in an oven at 120° C. for 30 minutes. The curing time could be reduced by increasing the catalyst concentration.

Figure 6:
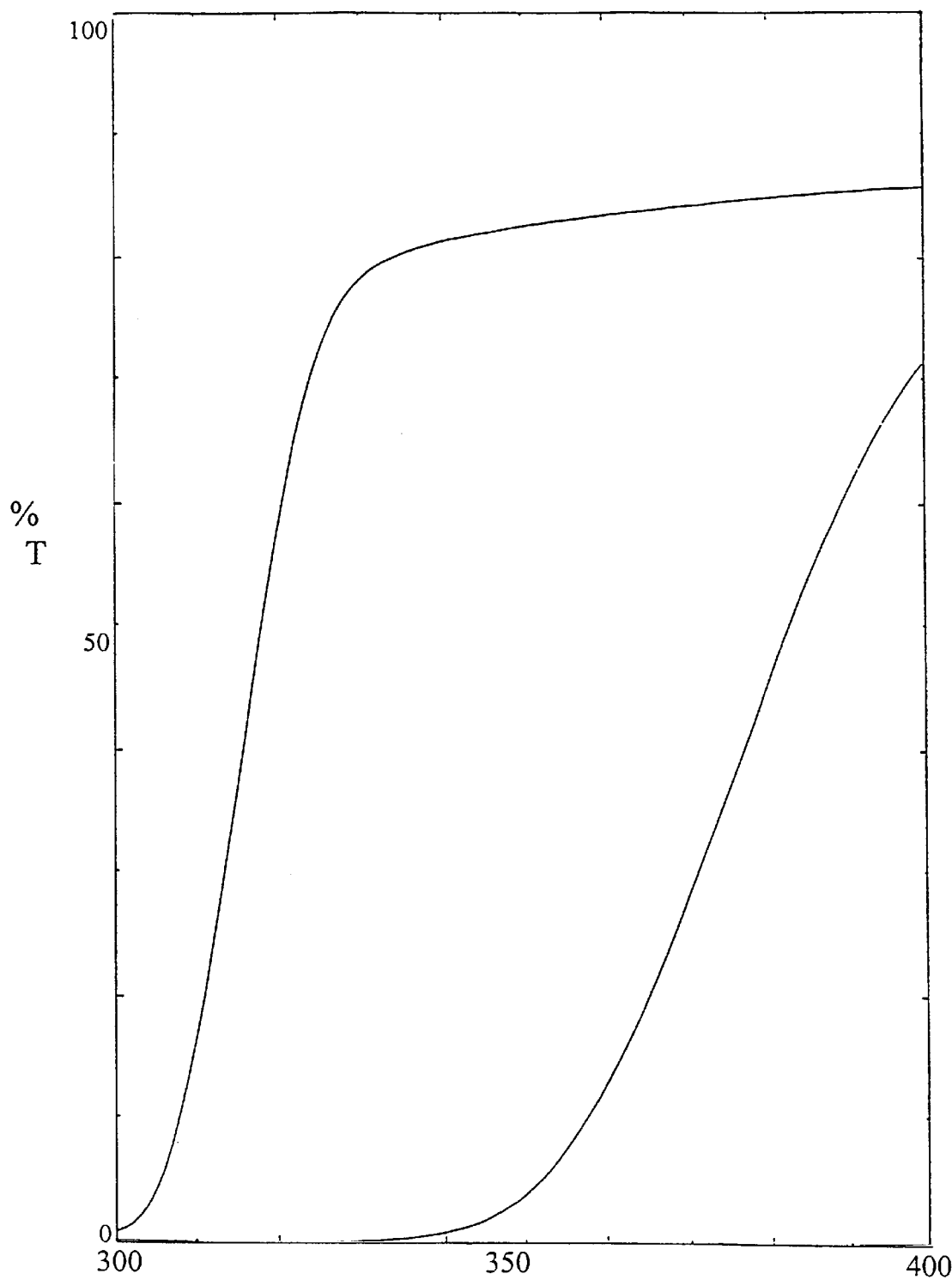
FIG. 6 is a graph of the transmission curves in the ultraviolet region between 300 and 400 nm wavelength of wire coated versus control polyester window film.

FIG. 6 shows the transmission curves as a function of wavelength of coated versus uncoated PET. It can be noted that PET film starts to absorb UV light below 330 nm due to which it undergoes UV degradation. The optically transparent coating on PET completely prevents UV penetration below 330 nm and protects the surface. The UV barrier can be increased by increasing either cerium oxide concentration or the coating thickness.

EXAMPLE 4

Eight grams of 20% cerium oxide were mixed with 6.66 g of 2 wt % hydroxypropylcellulose Klucel H (Aqualon Company) solution in water and 3.33 g of 10 wt % Klucel E in water and shaken vigorously. To this solution 0.233 g of 40 wt % MF resin in water was added as a crosslinker to heat cure HPC polymer. Heat curing of HPC with MF resin was catalyzed by adding 0.05 g of 1 wt % para-toluenesulfonic acid catalyst.

The mixture was shaken vigorously and was allowed to stand for 10 minutes for the foam to settle. Defoaming agent can be added to expedite this process. Also, a biocide can be added to prevent the biological degradation of HPC. The above solution was used to flow coat a 1-in. by 2-in. glass slide (Coming Glass Works). A clear coat was obtained which was dried and cured in an oven at 120° C. for 30 minutes. The curing time could be reduced by increasing the catalyst concentration.

Figure 7:
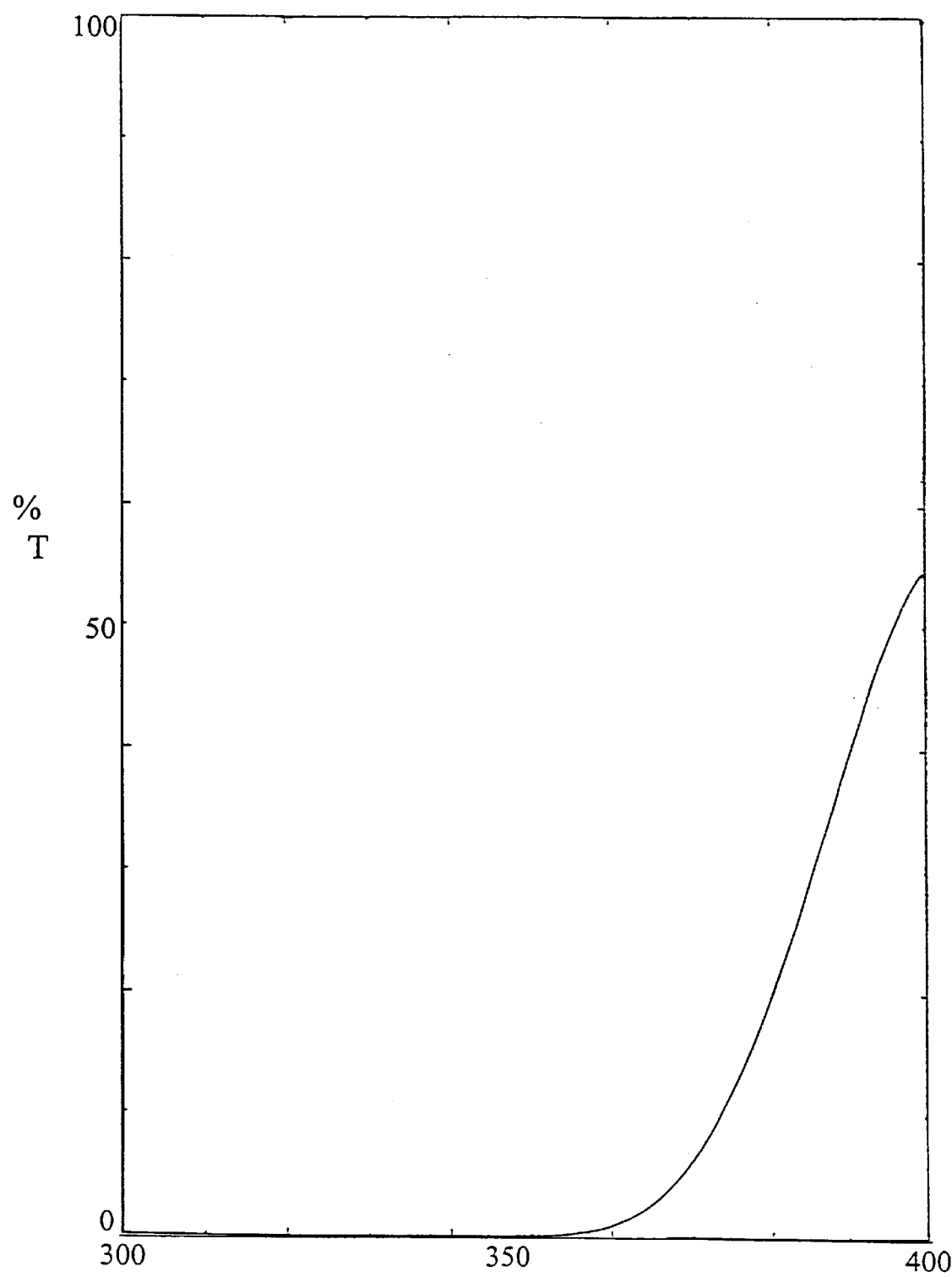
FIG. 7 is a graph of the transmission curve in the ultraviolet region of a flow coated glass slide.

FIG. 7 shows the transmission curve of the coated glass slide. The optically transparent coating completely blocks the ultraviolet light below 360 nm. The UV blockage can be increased by increasing either cerium oxide concentration or the coating thickness.

EXAMPLE 5

The solution as prepared in Example 4 was used to spin coat each side of a 2-in. by 2-in. window glass piece. The coated glass was then annealed at 400° C. to completely burn off the polymer and obtain a clear oxide film. The oxide film had mechanical integrity due to inter-particle and interface sintering.

Figure 8:
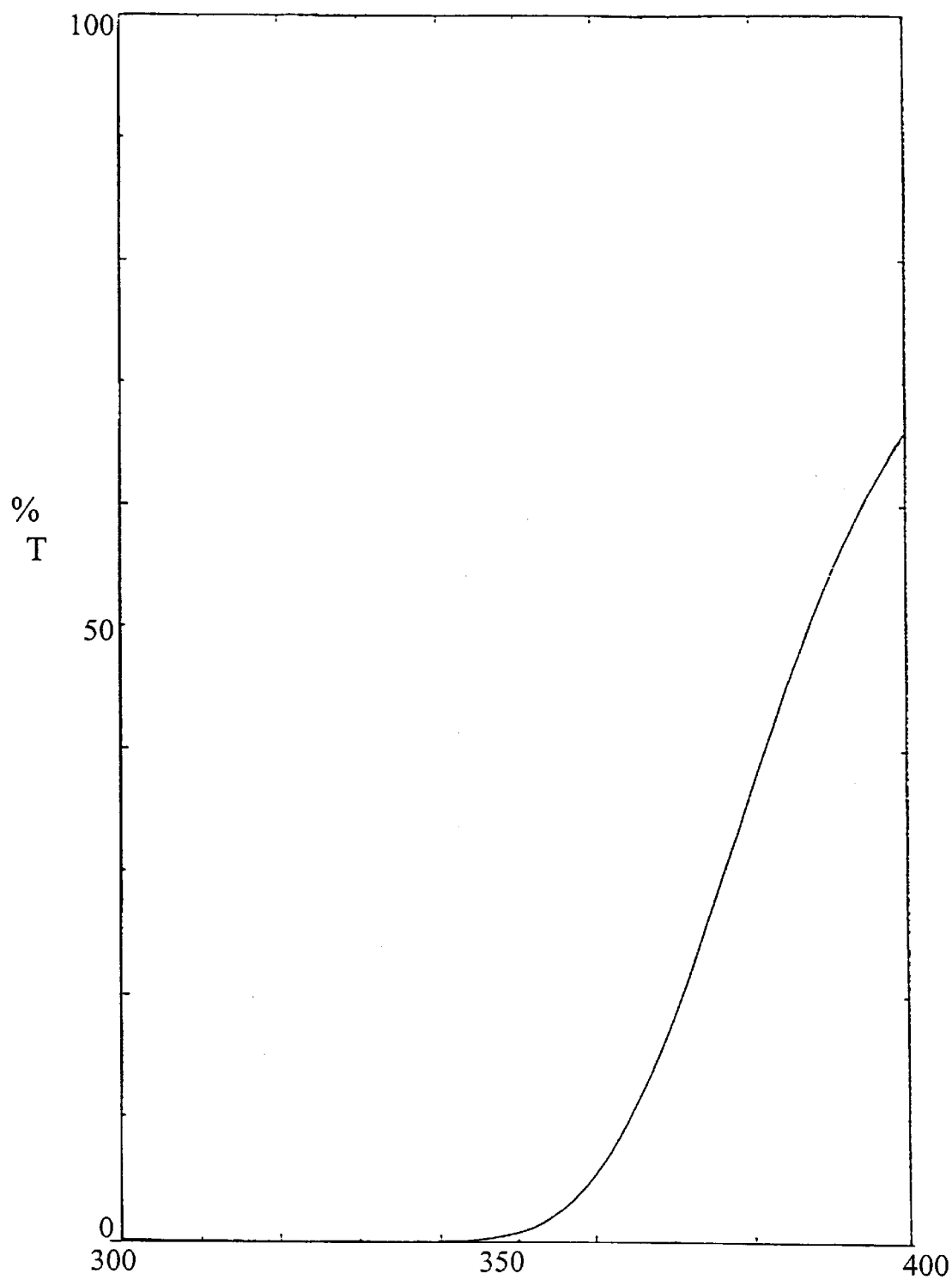
FIG. 8 is a graph of the transmission curve in the ultraviolet region of a spin coated window glass which was sintered at 400° C. to obtain a pure cerium oxide film.

In FIG. 8 it can observed that the cerium oxide coated glass completely blocks UV below 350 nm.

EXAMPLE 6

Figure 9:
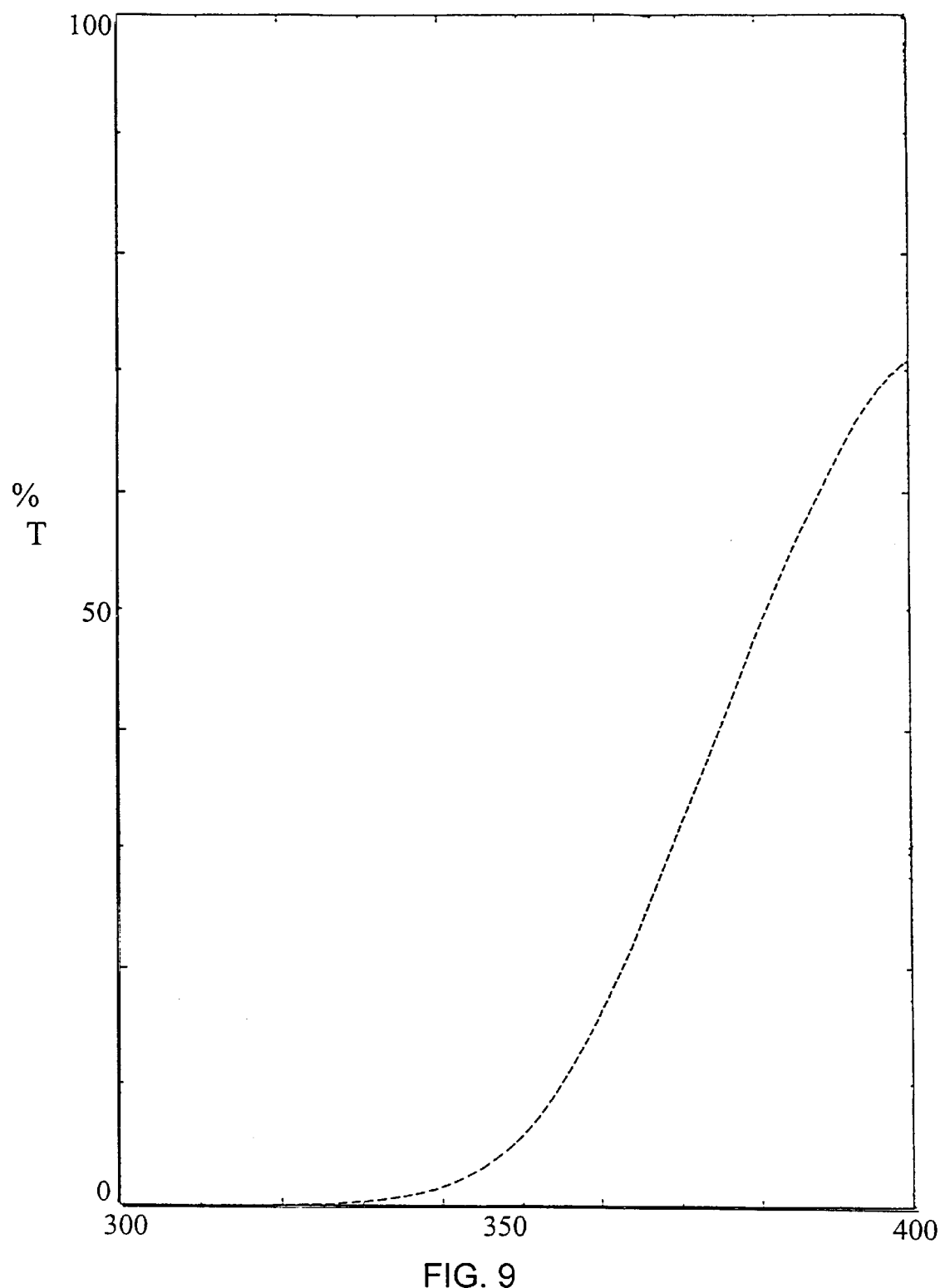
FIG. 9 is a graph of the transmission curve in the ultraviolet region of a hard abrasion resistant coating on polycarbonate.

Four grams of 20% ceria sol were mixed with 1 g 10 wt % Klucel E, 2.43 g 80% MF resin and 1.2 g water. To this solution 1 g of 1% acid catalyst and 0.66 g of 5% Byk 307 wetting agent was added. The mixture was stirred for 5 minutes and flow coated on a polycarbonate substrate. The air dried coating was cured in an oven at 130° C. for about 2 hours. A hard abrasion resistant transparent UV barrier coating resulted with excellent adhesion to polycarbonate. FIG. 9 shows that the coating completely blocks UV below 340 nm.

EXAMPLE 7

Figure 10:
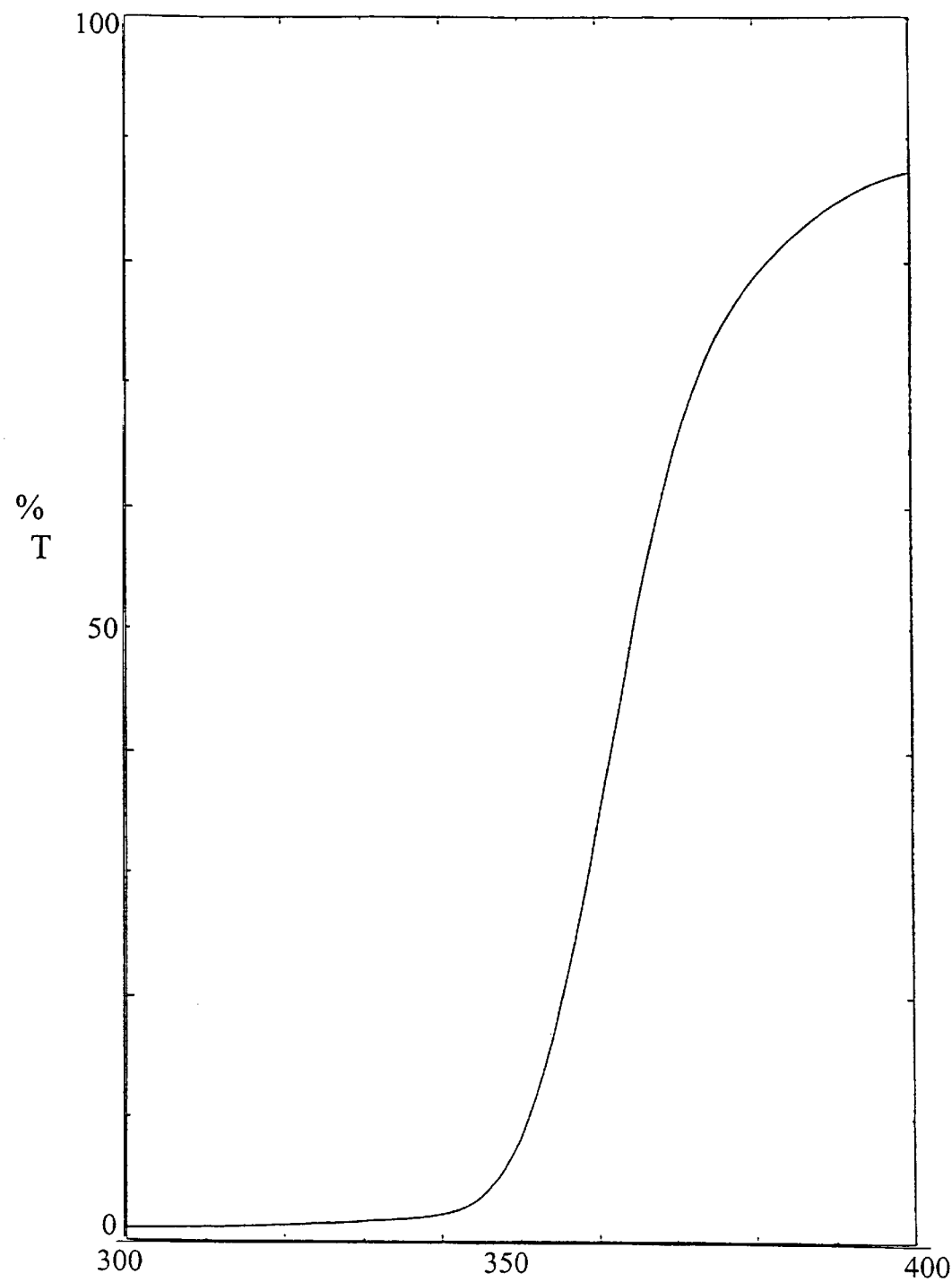
FIG. 10 is a graph of the transmission curve in the ultraviolet region of clear UV barrier glass with cerium oxide nano particles embedded in the matrix.

Seven hundred sixty-six grams of purified sand is mixed thoroughly with 35 g of 20% ceria sol containing 2% binder. The coated sand is dried and mixed with 149 g limestone and 85 g soda ash to obtain about 0.7 wt % cerium oxide in the final mixture. The mixture is melted to obtain 6.3 mm thick glass with embedded cerium oxide nano size particles. The glass so obtained is optically clear and has excellent UV barrier properties as seen in FIG. 10. The optical clarity of glass implies that the nano particles of cerium oxide remain stable in the matrix at the glass melt temperature.

EXAMPLE 8

Three grams of 20 wt % ceria sol were added in 0.75 g 2 wt % HPC solution and 0.75 g water and stirred for 30 minutes at room temperature. The resulting solution was used to spin coat a 1-in. diameter quartz substrate. The coated substrate was annealed at 1100° C. to completely burn off the polymer and obtain a clear oxide film. The oxide film had mechanical integrity due to inter-particle and interface sintering. The sintered film did not transmit light below 320 nm wavelength. The film remained clear and crack free even after 500 hours of annealing at 1100° C. This coating composition is well suited to coat high intensity discharge quartz lamps which have strong emission of UV light below 320 nm. The skin temperature of quartz casing of lit lamps rapidly reach 1100° C. and the UV barrier coating on such lamps should stay clear at that temperature for any practical use.

EXAMPLE 9

One gram of 20 wt % solution was added to 1 g 20% emulsified silanol terminated polydimethylsiloxane (Dow Coming). The silanol terminal ends were crosslinked using alkyltrialkoxysilane such as methyltriethoxysilane T4-0149 (DOW Corning). Alternatively, crosslinking can be achieved by using hydrogen terminated siloxanes such as Fluid 1107 (Dow Corning). The respective crosslinking reaction schemes can be illustrated as follows:

The crosslinking can be catalyzed by using metal salts such as zinc oleate, iron oleate and dibutyl tin laureate. This coating composition can be used to protect surfaces such as textiles, plastic, wood.

While the invention has been described in terms of its preferred embodiments, those skilled in the art will recognize that the invention can be practiced with considerable variation within the scope and spirit of the appended claims.

We claim:

1. A method for preparing a UV absorbing glass, consisting essentially of the steps of:
   admixing colloidal cerium oxide particles with particles of a glass-forming substance;
   binding said cerium oxide particles to said glass-forming particles so as to yield glass-forming particles having cerium oxide particles dispersed thereon; and
   melting and cooling the resulting glass-forming particles to form a UV absorbing glass.

* * * * *